(12) United States Patent
Knappe et al.

(10) Patent No.: US 10,835,473 B2
(45) Date of Patent: *Nov. 17, 2020

(54) FOAMING AGENT-CONTAINING COSMETIC COMPOSITIONS HAVING PIGMENT-CONTAINING STARCH PARTICULATES AND ANIONIC POLYMER

(71) Applicant: Henkel AG & Co. KGaA, Duesseldorf (DE)

(72) Inventors: Thorsten Knappe, Schenefeld (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,481

(22) Filed: Aug. 30, 2018

(65) Prior Publication Data

US 2019/0070092 A1 Mar. 7, 2019

(30) Foreign Application Priority Data

Sep. 1, 2017 (DE) .................... 10 2017 215 328

(51) Int. Cl.
*A61K 8/73* (2006.01)
*A61K 8/04* (2006.01)
*A61K 8/02* (2006.01)
*A61K 8/19* (2006.01)
*A61K 8/81* (2006.01)
*A61Q 5/02* (2006.01)
*A61Q 5/06* (2006.01)

(52) U.S. Cl.
CPC ............ *A61K 8/732* (2013.01); *A61K 8/0241* (2013.01); *A61K 8/046* (2013.01); *A61K 8/19* (2013.01); *A61K 8/8141* (2013.01); *A61Q 5/02* (2013.01); *A61Q 5/065* (2013.01); *A61K 2800/43* (2013.01)

(58) Field of Classification Search
CPC ...... A61K 8/732; A61K 8/0241; A61K 8/046; A61K 8/19; A61K 8/8141; A61K 2800/43; A61Q 5/02; A61Q 5/065
See application file for complete search history.

(56) References Cited

U.S. PATENT DOCUMENTS 4,423,199 A * 12/1983 Chang .................. A61K 8/8158
526/307.6
7,455,848 B2 * 11/2008 Hessefort ............. A61K 8/8158
424/401
(Continued)

FOREIGN PATENT DOCUMENTS

WO 2013186715 A2 12/2013
WO 2018177722 A1 10/2018

OTHER PUBLICATIONS

Aaserud D.J et. al.; "Gel Permeation Chromatography Coupled to Fourier Transform Mass Spectrometry for Polymer Characterization"; Anal. Chem. 1999, 71, 4793-4799.
Neelam et al., "Various Techniques for the Modification of Starch and the Applications of its Derivatives", International Research Journal of Pharmacy, Review Article, 2012, 3 (5), pp. 25-31, Bareilly, India.

* cited by examiner

*Primary Examiner* — Robert A Wax
*Assistant Examiner* — Olga V. Tcherkasskaya
(74) *Attorney, Agent, or Firm* — Lorenz & Kopf, LLP

(57) ABSTRACT

The present disclosure relates to cosmetic compositions for the cleaning of keratinic fibers. An exemplary cosmetic composition includes, based on the total weight of the cosmetic composition, a) a particulate comprising, based on the total weight of the particulate, a1) from about 65 to about 98% by weight of a starch, and a2) from about 1.0 to about 3.0% by weight of a pigment, b) an anionic polymer comprising structural units of the formula (I), the formula (II), and the formula (III):

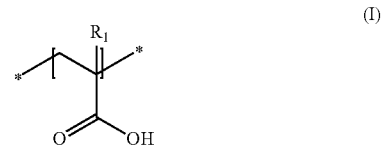

(I)

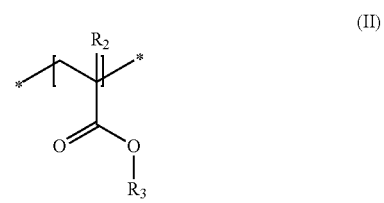

(II)

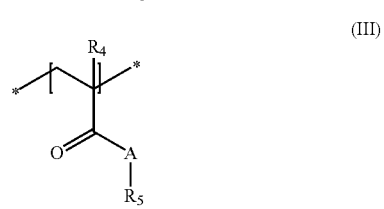

(III)

wherein $R_1$, $R_2$ and $R_4$, each independently of one another, stand for a hydrogen atom or a $C_1$-$C_4$ alkyl group, $R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group, A stands for oxygen, sulfur or an NH group, and c) a foaming agent.

20 Claims, No Drawings

(56) References Cited

U.S. PATENT DOCUMENTS

| | | | |
|---|---|---|---|
| 8,105,393 B2* | 1/2012 | Suddaby | A61K 8/19 |
| | | | 132/202 |
| 9,181,436 B2* | 11/2015 | Kitagawa | A61K 8/0241 |
| 2011/0070273 A1* | 3/2011 | Zheng | A61K 8/0204 |
| | | | 424/401 |
| 2011/0168200 A1* | 7/2011 | Bourdin | A61K 8/0216 |
| | | | 132/202 |
| 2012/0207694 A1 | 8/2012 | Mueller et al. | |
| 2014/0150186 A1 | 6/2014 | Metten et al. | |
| 2014/0283865 A1* | 9/2014 | Avery | A61Q 5/02 |
| | | | 132/202 |
| 2015/0297521 A1* | 10/2015 | To | A61K 31/216 |
| | | | 427/213 |

FOAMING AGENT-CONTAINING COSMETIC COMPOSITIONS HAVING PIGMENT-CONTAINING STARCH PARTICULATES AND ANIONIC POLYMER

CROSS-REFERENCE RELATED APPLICATION

This application claims priority to German Patent Application No. 10 2017 215 328.8, filed Sep. 1, 2017, which is incorporated herein by reference in its entirety.

TECHNICAL FIELD

The application pertains to the technical field of cleaning of keratin-comprising materials, in particular human hair. The subject of the application is cosmetic compositions comprising at least one pigment-comprising starch particulate, at least one special anionic polymer and at least one foaming agent. Furthermore, the subject of the present application is methods for cleaning the hair using these agents and the use of these agents for the cleaning of keratinous fibers.

BACKGROUND

The cleaning of keratin-comprising fibers is usually based on the combined effect of water, soap and mechanical work on the fiber. Thus, for example, during hair washing, a surfactant-comprising shampoo is first applied to the damp hair and massaged into the hair. If the hair is subsequently rinsed with water, the dissolved impurities are rinsed out of the hair by the water, the shampoo and/or the mechanical action and the hair is cleaned in this way.

If there is no water available for hair cleaning or if classic hair washing is not possible due to lack of time, hair cleaning by employing a dry shampoo is used as an alternative to water-based hair cleaning.

Dry shampoos contain, as an essential active ingredient, particulate carrier material, which due to its adsorption properties, is able to bind to impurities located on the hair or scalp, such as fats or sebum. Optionally modified starches are used in particular as carrier material. If the hair is combed or brushed after the application of the dry shampoo, the adsorbed impurities are removed from the hair with the powdered carrier material.

A preferred ready-made form for dry shampoos is the aerosol spray. In the case of corresponding products, the powder suspended in a liquid phase is sprayed onto the hair by employing a foaming agent.

Dry shampoo incompletely removed from the hair can cause a gray film on the hair or stick on the hair in the form of visible particulates. Both effects are among the main disadvantages of the use of dry shampoos. As a solution to this technical problem, the prior art has proposed the use of a combination of starch and clays as a particulate carrier material. However, this technical solution has proven to be less than ideal. On the one hand, the problem of gray film formation can not be completely eliminated by this technical approach; on the other hand, the use of a mixture of particulate carrier materials increases the complexity and cost of the cosmetic product and leads to difficulties in application, in particular in the packaging of an aerosol spray.

For many users of dry shampoos, apart from a high cleaning performance, there is also the desire for additional styling and color effects, for example, increased volume, improved hair texture and temporary hair coloring, through the use of these shampoos, so that the additional use of styling products and products for temporary hair coloring can be dispensed with. Such styling effects can be achieved by the use of film formers, the use of pigments is known for temporary hair coloring. However, the use of these film formers can lead to clogging of the aerosol sprays, since there may be clumping of the particulate carrier due to the water content entrained by the film former. The pigments used often do not sufficiently adhere to the fibers and are particularly removed by the action of external environmental influences, such as rain, sweat and abrasion.

The object of the present application was therefore to provide a dry shampoo having high cleaning performance and good application properties when applied as an aerosol spray, which leads to a high volume and/or an improved hair texture when applied and these effects also have a high long-term effect. In addition, no visible residue or gray film should remain on the hair after the application. Rather, a water-resistant temporary hair coloring should be achieved.

BRIEF SUMMARY

Cosmetic compositions for the cleaning of keratinic fibers are provided. An exemplary cosmetic composition includes, based on the total weight of the cosmetic composition, a) a particulate comprising, based on the total weight of the particulate, a1) from about 65 to about 98% by weight of a starch, and a2) from about 1.0 to about 3.0% by weight of a pigment, b) an anionic polymer comprising structural units of the formula (I), the formula (II), and the formula (III):

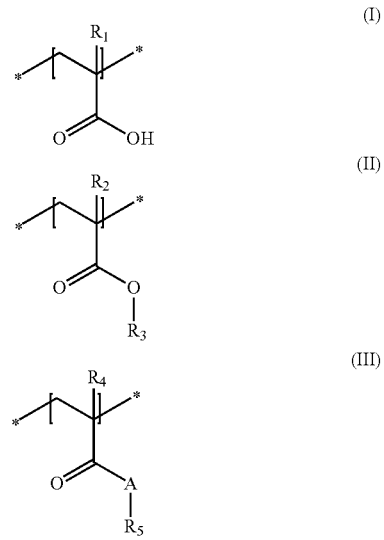

wherein $R_1$, $R_2$ and $R_4$, each independently of one another, stand for a hydrogen atom or a $C_1$-$C_4$ alkyl group, $R_3$ stands for a branched or unbranched, saturated or unsaturated $C_1$-$C_{12}$ alkyl group, $R_5$ stands for a branched or unbranched, saturated or unsaturated $C_6$-$C_{14}$ alkyl group, A stands for oxygen, sulfur or an NH group, and c) a foaming agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has been shown that these objects can be achieved by the combination of pigment-comprising starch as a carrier material and a special anionic polymer. This polymer is readily soluble in anhydrous solvents but need not be neutralized for high film-forming properties. Consequently, the use of this polymer does not produce any undesired introduction of water, which leads to a clumping of the carrier material and thus to a clogging of the aerosol nozzle. In addition, this anionic polymer has no negative influence on the cleaning effect of the pigment-comprising starch, so that in addition to the high styling effect, excellent cleaning performance can be achieved. In addition, this combination does not lead to visible residues or gray film remaining on the hair after the application of the composition as contemplated herein. Rather, a temporary coloring of the hair can be achieved by using a starch that contains pigments. Due to the high water resistance of the anionic polymer, the styling effects achieved, in particular a high volume and/or improved hair texture and the temporary coloration, are therefore guaranteed even at high humidity or exposure to water, sweat and abrasion over a long period and can only be removed by using surfactant-comprising cleaning agents.

A first subject of the present disclosure is thus a cosmetic composition comprising, based on its total weight,
a) at least one particulate comprising, based on its total weight,
 a1) from about 65 to about 98% by weight of at least one starch and
 a2) from about 1.0 to about 3.0% by weight of at least one pigment,
b) at least one anionic polymer comprising at least one structural unit of the formula (I) and at least one structural unit of the formula (II) and at least one structural unit of the formula (III)

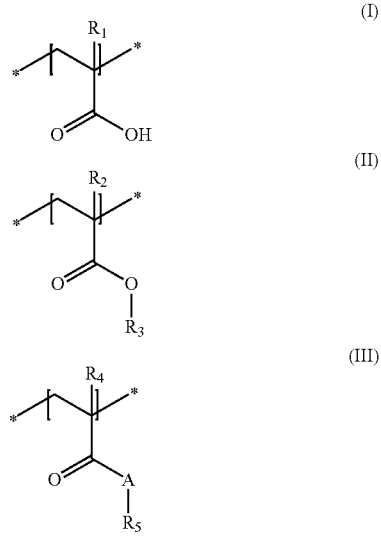

wherein
$R_1$, $R_2$ and $R_4$, each independently of one another, stand for a hydrogen atom or a $C_1$-$C_4$ alkyl group,
$R_3$ stands for a branched or unbranched, saturated or unsaturated $C_1$-$C_{12}$ alkyl group,
$R_5$ stands for a branched or unbranched, saturated or unsaturated $C_6$-$C_{14}$ alkyl group,
A stands for oxygen, sulfur or an NH group and
c) at least one foaming agent.

According to the above formulas and all the following formulas, a chemical bond which is designated with the symbol "*" stands for a free valence of the corresponding structural fragment. Here, free valence is to be understood as meaning the number of atomic bonds which emanate from the corresponding structural fragment at the position indicated by the symbol "*". In the context of the present disclosure, in each case an atomic bond preferably emanates from the positions of the structural fragments designated with the symbol "*" to further structural fragments.

Particulate solids are understood to be "particulates" at about 25° C. and about 1013 mbar. For the purposes of the present disclosure, pigments are understood to mean coloring compounds which have a solubility of less than about 0.1 g/l at about 20° C. in water. The water solubility can be carried out, for example, by employing the method described below: about 0.1 g of the pigment is weighed in a beaker. A stir bar is added. It is then filled up to about 1 l with distilled water (about 20° C.). It is stirred for an hour. If undissolved components of the pigment are still visible in the mixture after this period, the solubility of the pigment is below about 0.1 g/l.

In the context of the present disclosure, the term "anionic polymers" is understood to mean those polymers which carry at least one structural unit having permanently anionic groups in a protic solvent under standard conditions, wherein the anionic groups have to be compensated by counterions while maintaining the electroneutrality. Carboxyl groups in particular fall under anionic groups.

The specification % by weight refers in the present case, unless stated otherwise, to the total weight of the cosmetic composition as contemplated herein, wherein the sum of all ingredients of the composition as contemplated herein results in about 100% by weight.

As the first essential constituent a), the cosmetic agent as contemplated herein contains at least one particulate as a first essential component a), comprising at least one starch a1) and at least one pigment a2).

Starch is a reserve carbohydrate which is stored by many plants in the form of starch grains (granules), which are usually from about 1 μm to about 200 μm in size, in various parts of plants, for example, in tubers or roots, grain seeds, fruits and in the marrow. Starch belongs to the family of homoglycans and is a polycondensation product of D-glucose. Preferred starches as contemplated herein are selected from at least one polycondensation product of D-glucose obtained from native and/or physically modified starch from potatoes, maize, rice, peas, acorns, chestnuts, barley, wheat, bananas, sago, millet, sorghum, oats, rye, beans, sweet potatoes, maranta or manioc and their mixtures. In terms of cleaning performance, the use of native and/or physically modified rice starch has proven to be particularly advantageous. A native starch is understood to mean a starch which is isolated from starch-comprising plants and which has not been physically or chemically modified after isolation and cleaning. On the other hand, physically modified starch is understood to mean a starch which has undergone at least one physical modification after isolation. Physical modification here is understood to mean the modification using pressure and/or heat and/or light. However, a modification by employing chemical and enzymatic reactions, for example, the hydrolysis of the starch, does not fall under the term of physical modification. A preferred used physical modification is the use of heat, especially the cooking of the native starch. Preferred embodiments of the present disclosure are therefore exemplified in that the particulate a) contains at least one starch a1) selected from chemically and/or physically modified rice starches, in particular from physically modified rice starch. A particularly high adhesion of the pigments to the starch is achieved through the use of native and/or physically modified rice starches, so that in addition to the excellent cleaning performance, a long-lasting temporary hair coloring is also possible.

It has been found as contemplated herein that the composition of the starch particulates has proven itself to be relevant for the cosmetic effect. Therefore, preferably used particulates a) have a certain proportion of native and/or physically modified starch, in particular rice starch. It is thus preferred as contemplated herein when the at least one particulate a) contains the at least one starch a1), in particular the physically modified rice starch, in a total amount from about 70 to about 96% by weight, in particular from about 80 to about 94% by weight, respectively based on the total weight of the particulate. The use of particulates which contain a high proportion by weight of physically modified rice starch leads to a particularly high cleaning performance of the cosmetic agent, but without the long-lasting styling effects achieved by the anionic polymer, in particular the high volume and/or the improved hair texture, and without negatively influencing the temporary hair coloring.

The particulates a) contained in the cosmetic compositions furthermore have at least one pigment a2) in addition to the previously mentioned starch a1). In principle, all types of water-insoluble pigments are suitable, for example, natural inorganic pigments (also referred to as mineral pigments). These pigments mainly contain sulfides and oxides.

Examples of such pigments are ocher (Fe(OOH), Pigment Yellow 43), baked Siena ($Fe_2O_3$, Pigment Red 102), Umbra ($Fe_2O_3 \times MnO_2$; Pigment Brown), Cinnabar (β-HgS, PR 106), lapis lazuli (ultramarine, $Na_6Al_6Si_6O_{24} \times Na_2Sn$; Pigment Blue 29), azurite (basic copper carbonate, $Cu_3[OH/CO_3]_2$; PB 30), green earth (FeO-comprising silicate, Pigment Green 23), malachite ($Cu_2[(OH)_2, CO_3]$) and carbon black (carbon (graphite), Pigment Black 9). However, the use of synthetic inorganic pigments has proven to be advantageous with regard to the avoidance of undesirable visible residues or gray film or the water-resistant temporary coloring of the fibers. Synthetic inorganic pigments are produced, for example, by chemical and/or physical conversion (decomposition, precipitation, annealing). These include in particular white pigments (titanium dioxide ($TiO_2$), Pigment White PW 6, zinc sulfide (ZnS), PW 7; zinc oxide (ZnO), PW 4; antimony white ($Sb_2O_3$), PW 11, lithopone ($ZnS/BaSO_4$), PW 5; Lead white ($2PbCO_3 \times Pb(OH)_2$), PW 1), subordinate white fillers (calcium carbonate, PW 18; talc, PW 26 and barium sulfate, PW 21);

black pigments (manganese black, spinel black and carbon blacks (graphite carbon);

luster pigments (absorption pigments, metal pigments or metallic effect pigments and pearlescent pigments) and inorganic colored pigments (iron oxide pigments, iron blue pigments, ultramarine pigments and, due to their toxicological properties, less suitable lead chromate pigments, chromium oxide pigments, cadmium pigments and bismuth vanadate pigments).

Preferred synthetic inorganic pigments are metal pigments or metallic effect pigments of powdery metals or metal alloys, such as aluminum bronzes (metal: Al), gold bronzes (metal: Cu, Cu—Al or Cu—Zn alloy), silver bronzes (metal: Cu—Zn—Ni), fire-colored bronzes (metal: oxidized Cu—Zn) and patent bronzes (metal: Cu—Zn—(Ni)+dye).

Further preferred synthetic inorganic pigments are pearlescent pigments, which consist of several layers with different refractive indices. Examples of such pearlescent pigments are magnesium stearate, zinc stearate and lithium stearate or ethylene glycol distearate or polyethylene terephthalate and pearlescent pigments which consist essentially of mica, titanium dioxide (titanium dioxide mica), bismuth chloride oxide or guanine, and furthermore can be coated with colored oxide layers (for example, iron oxides or chromium oxides). Pearlescent pigments based on mica and on mica/metal oxide are, as contemplated herein, particularly preferred pearlescent pigments. Mica belongs to the layered silicates. The most important representatives of these silicates are muscovite, phlogopite, paragonite, biotite, lepidolite and margarite. To prepare the pearlescent pigments in conjunction with metal oxides, the mica, predominantly muscovite or phlogopite, is coated with a metal oxide. Suitable metal oxides are $TiO_2$, $Cr_2O_3$ and $Fe_2O_3$. Interference pigments and color luster pigments are obtained as pearlescent pigments preferred as contemplated herein through appropriate coating. In addition to a glittering optical effect, these pearlescent pigment types also have color effects. Furthermore, the pearlescent pigments which can be used as contemplated herein may additionally contain a color pigment which does not derive from a metal oxide.

Very particularly preferred pearlescent pigments are pigments which are sold by Merck under the trademark Colorona®, wherein the pigments Colorona® red-brown (from about 47-about 57% by weight Muscovite Mica ($KH_2(AlSiO_4)_3$), from about 43-about 50% by weight $Fe_2O_3$ (INCI: iron oxides CI 77491), <about 3% by weight $TiO_2$ (INCI: titanium dioxide CI 77891), Colorona® Blackstar Blue (from about 39-about 47% by weight Muscovite mica ($KH_2(AlSiO_4)_3$), from about 53-about 61% by weight $Fe_3O_4$ (INCI: iron oxides CI 77499)), Colorona® Siena Fine (from about 35-about 45% by weight Muscovite mica ($KH_2(AlSiO_4)_3$), from about 55-about 65% by weight Fe2O3 (INCI: iron oxides CI 77491)), Colorona® Aborigine Amber (from about 50-about 62% by weight Muscovite mica ($KH_2(AlSiO_4)_3$), from about 36-4 about 4% by weight Fe3O4 (INCI: iron oxides CI 77499), from about 2-6 about % by weight TiO2 (INCI: titanium dioxide CI 77891)), Colorona® Patagonian Purple (from about 42-about 54% by weight Muscovite mica ($KH_2(AlSiO_4)_3$), from about 26-about 32% by weight Fe2O3 (INCI: iron oxides CI 77491), from about 18-about 22% by weight $TiO_2$ (INCI: titanium dioxide CI 77891), from about 2-about 4% by weight Prussian blue (INCI: ferric ferrocyanide CI 77510)), Colorona® Chameleon (from about 40-about 50% by weight Muscovite mica ($KH_2(AlSiO_4)_3$), from about 50-about 60% by weight $Fe_2O_3$ (INCI: iron oxides CI 77491)) and Silk® Mica (>about 98% by weight Muscovite mica ($KH_2(AlSiO_4)_3$)) are particularly preferred.

One group of particularly preferred pigments are the coloring synthetic iron oxides. Particularly preferred representatives of this substance class are Pigment Brown 6 (CI No 77491), Pigment Red 101 (CI No 77491), Pigment Yellow 42 (CI No 77492), Pigment Black 11 (CI No 77499) and mixtures of these pigments. Preferred embodiments of the first present disclosure subject are therefore exemplified in that the at least one particulate a) contains at least one pigment a2) selected from synthetic inorganic pigments, preferably from synthetic inorganic pigments from the group of metal oxides, in particular from synthetic inorganic pigments from the group of iron oxides. The use of these pigments in conjunction with the specific starch mentioned above leads to a high cleaning performance and a good temporary hair coloring. By adding the anionic polymer b), the temporary color achieved can not only be protected against the action of external environmental influences, but water-resistant styling effects are also additionally achieved.

With regard to the cleaning effect of the cosmetic composition and the temporary hair coloring, it has proven to be advantageous when the particulates a) contain the pigment a2), in particular the above-mentioned synthetic inorganic pigments from the group of iron oxides, in a certain proportion. It is therefore advantageous as contemplated herein when the at least one particulate a) contains at least one pigment a2), in particular the synthetic inorganic pigment from the group of iron oxides, in a total amount from about 1.5 to about 25% by weight, in particular from about 3.5 to about 18% by weight, respectively based on the total weight of the particulate. The use of such amounts of pigment ensures a sufficient temporary coloring of the hair during the cleaning with the compositions as contemplated herein, but also a sufficiently high level of starch in order to achieve a satisfactory cleaning effect.

In addition to the starch a1), in particular the physically modified rice starch, and the pigment a2), in particular the synthetic inorganic pigments from the group of iron oxides, the particulates may contain other ingredients. Such ingredients prevent a clumping of the particulates a) in the cosmetic agent and thus clogging of the aerosol nozzles, so that a complete emptying of the container is made possible. Liquid silicone oils have proven to be advantageous in this context. Liquid silicone oils are understood to mean silicone oils which are liquid at about 20° C. and about 1013 hPa. It is therefore preferred as contemplated herein when the at least one particulate a) additionally contains at least one liquid silicone oil a3) selected from the group of dialkyl and alkylaryl siloxanes, preferably from the group of polydimethylsiloxane, cyclopentasiloxane, cyclohexasiloxane and methylphenylpolysiloxane, in particular from polydimethylsiloxanes. The use of polydimethylsiloxanes has proven to be particularly advantageous with regard to the prevention of the clumping of the particulates a).

In this context, it is preferred when the at least one liquid silicone oil a3), in particular polydimethylsiloxane, is present in certain proportions in the particulates a). It is therefore advantageous as contemplated herein when the at least one liquid silicone oil a3), in particular polydimethylsiloxane, is present in a total amount from about 0.5 to about 5.0% by weight, in particular from about 1.5 to about 3.0% by weight, respectively based on the total weight of the particulate.

In addition to the above-mentioned liquid silicone oils a3), the use of cationic surfactants has proven to be particularly advantageous with regard to avoiding clumping of the particulates a). A preferred embodiment of this present disclosure subject is therefore exemplified in that the at least one particulate a) additionally contains at least one cationic surfactant a4) selected from the group of quaternary ammonium compounds, preferably from the group of cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, in particular from cetyltrimethylammonium chloride. The use of cetyltrimethylammonium chloride has proven to be particularly advantageous with regard to the prevention of the clumping of the particulates a).

In this context, it is preferred when the at least one cationic surfactant a4), in particular cetyltrimethylammonium chloride, is present in certain proportions in the particulates a). It is therefore advantageous as contemplated herein when the at least one cationic surfactant a4), in particular cetyltrimethylammonium chloride, is present in a total amount from about 0.01 to about 1.0% by weight, in particular from about 0.05 to about 0.5% by weight, respectively based on the total weight of the particulate.

Particulates a) preferably used as contemplated herein preferably have a core of the above-mentioned starch a1) and a pigment coating of previously mentioned pigments a2), which at least partially surrounds this core. The starch particulates are preferably prepared by coating the starch with the pigment. Particularly preferred embodiments of the first subject present disclosure subject are therefore exemplified in that the at least one particulate a) is a particulate of the at least one starch a1) coated with the at least one pigment a2), in particular a particulate of the at least one physically modified rice starch coated with at least one synthetic inorganic pigment from the group of iron oxides. The use of particulates a) in which the physically modified rice starch is at least partially coated with synthetic inorganic pigments from the group of iron oxides, in addition to a high cleaning performance, also leads to a high temporary coloring of the treated keratinic fibers. Not only an additional styling effect, but also a high water resistance of the temporary hair coloring and the styling effect can be achieved by the addition of the anionic polymer b).

With regard to the cleaning performance and the good applicability and the complete emptying of the container, it has proven to be advantageous when the particulates a), in particular with the previously mentioned ingredients, have a certain mean particulate size D50. Preferred embodiments of the first present disclosure subject are therefore exemplified in that the at least one particulate a) has a mean particulate size D50 from about 0.5 to µm about 50 µm, preferably from about 2.0 µm to about 40 µm, more preferably from about 4.0 µm to about 30 µm, in particular from about 5.0 µm to about 20 µm. The mean particulate sizes mentioned above can be determined, for example, by employing dynamic light scattering (DLS).

Particularly preferably used particulates a) are therefore exemplified in that they, based on their total weight,
- contain from about 70 to about 96% by weight of a physically modified rice starch,
- contain from about 1.5 to about 25% by weight of synthetic inorganic pigment from the group of iron oxides,
- contain from about 1.5 to about 3.0% by weight of polydimethylsiloxane,
- contain from about 0.05 to about 0.5% by weight of cetyltrimethylammonium chloride.

Further particularly preferably used particulates a) are exemplified in that they, based on their total weight,
- contain from about 70 to about 96% by weight of a physically modified rice starch,
- contain from about 1.5 to about 25% by weight of synthetic inorganic pigment from the group of iron oxides,
- contain from about 1.5 to about 3.0% by weight of polydimethylsiloxane,
- contain from about 0.05 to about 0.5% by weight of cetyltrimethylammonium chloride and have a mean particulate diameter $D_{50}$ from about 5.0 to about 20 µm.

Preferred cosmetic compositions as contemplated herein contain the at least one particulate a) in a total amount from about 1.0 to about 10% by weight, preferably from about 1.0 to about 8.0% by weight, more preferably from about 1.5 to about 6.0% by weight, in particular from about 1.5 to about 5.0% by weight, respectively based on the total weight of the composition. The use of the abovementioned total amount of particulates a), in particular of particulates a) having the abovementioned properties, has proven to be advantageous, in particular with regard to the applicability and the cleaning performance. In addition, the use of the particulates a) in the previously mentioned total amounts leads to a high temporary hair coloring. Furthermore, the use of these total amounts achieves the styling effect through the anionic polymer b), in particular the high volume and/or the improved texture, and the high water resistance of the coloring and the styling effect is not negatively affected.

As a second essential constituent b), the cosmetic agent as contemplated herein contains at least one anionic polymer which contains at least one structural unit of the formulas (I) to (III). In the structural units of the formulas (I) to (III), the radicals $R_1$, $R_2$ and $R_4$ can stand for $C_1$-$C_4$ alkyl groups. Examples of such groups are methyl, ethyl, propyl, isopropyl, hydroxypropyl, butyl, sec-butyl, isobutyl, tert-butyl and hydroxybutyl groups. Furthermore, the radicals $R_3$ and $R_5$ in the structural units of the formulas (II) and (III) can stand for $C_1$-$C_{12}$ or $C_6$-$C_{14}$ alkyl groups. Such groups are, for example, pentyl, hexyl, heptyl, capryl, caprine, lauryl and myristyl groups.

In the context of the present disclosure, it is preferred for the radicals $R_1$, $R_2$ and $R_4$ in the formulas (I) to (III) to stand for certain groups. Preferred embodiments of this present disclosure subject are therefore exemplified in that in the structural units of the formulas (I) and (III) the radicals $R_1$ and $R_4$, in each case independently of one another, stand for a hydrogen atom and in the structural unit of the formula (II), the radical $R_2$ stands for a methyl group. Therefore, anionic polymers based on acrylic acid, methacrylates and acrylamides or acrylates are preferably used. The use of such anionic polymers leads to a particularly high water resistance of the styling effect achieved and the temporary hair coloring.

Furthermore, it has proven to be advantageous in the context of the present disclosure when the radical $R_3$ in the structural unit of the formula (II) stands for certain groups. It is therefore preferred that in the structural unit of the formula (II), the radical $R_3$ stands for a branched $C_3$-$C_6$ alkyl group, in particular a *—$CH_2$—$CH(CH_3)_2$ group. Here, the * symbol indicates the linkage of the radical $R_3$ with the oxygen atom of the structural unit of the formula (II). The radical $R_3$ is thus bonded via the $CH_2$ group to the carbonyl group of the structural unit of the formula (II). The use of anionic polymers, which in particular contain branched methacrylates, has proven to be particularly advantageous with regard to the water resistance of the styling effect achieved and the temporary hair coloring.

Furthermore, it is preferred as contemplated herein when A in the structural unit of the formula (III) stands for an NH group. Preferred anionic polymers therefore contain at least one structural unit based on acrylamides. The use of anionic polymers based on acrylamides leads to an improved resistance against external environmental influences, but without negatively influencing the cleaning performance of the particulates a).

Furthermore, it has proven to be advantageous in the context of the present disclosure when the radical $R_5$ in the structural unit of the formula (III) stands for certain groups. It is therefore preferred as contemplated herein when, in the structural unit of the formula (III), the radical $R_5$ stands for a branched $C_6$-$C_{10}$ alkyl group, in particular a *—$C(CH_3)_2$—$CH_2$—$C(CH_3)_3$ group. Here, the * symbol indicates the linkage of the radical $R_5$ with the unit A of the structural unit of the formula (III). The use of anionic polymers, which in particular contain branched acrylamides and acrylates, has proven to be particularly advantageous with regard to the water resistance of the styling effect achieved and the temporary hair coloring.

Accordingly, anionic polymers which contain at least one structural unit of the formula (I), at least one structural unit of the formula (II) and at least one structural unit of the formula (III) are particularly preferably used as contemplated herein

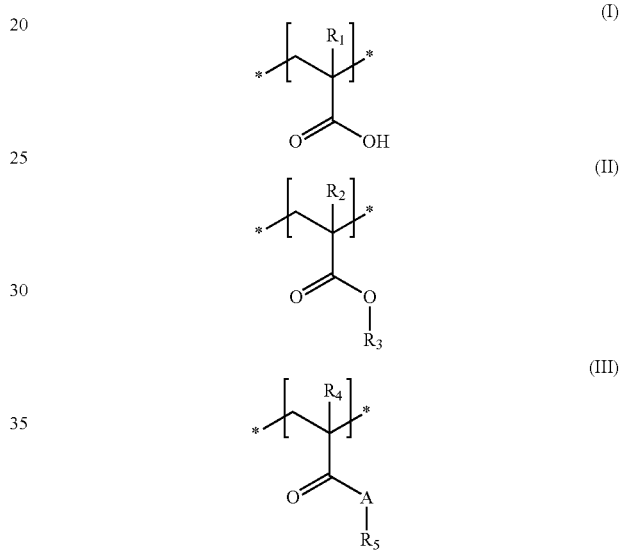

wherein
$R_1$ and $R_4$ each stand for a hydrogen atom,
$R_2$ stands for a methyl group,
$R_3$ stands for a *—$CH_2$—$CH(CH_3)_2$ group,
$R_5$ stands for a *—$C(CH_3)_2$—$CH_2$—$C(CH_3)_3$ group and
A stands for an NH group The use of such anionic polymers based on acrylic acid, 2-methylpropyl methacrylate and octylacrylamide has proven to be particularly advantageous in terms of the durability of the styling effect achieved and the temporary hair coloring against external environmental influences. The combination of particulates a), in particular the abovementioned special particulates a), with the special anionic polymers b) not only leads to a high cleaning performance, but also to long-lasting and water-resistant styling effects, in particular an increased volume and/or an improved hair texture, and temporary hair colorings.

Preferably used anionic polymers have certain mean molecular weights $M_w$. The determination of these molecular weights can be carried out, for example, by coupling a gel permeation chromatography (GPC) to a Fourier transform mass spectrometer (FTMS) as described in Aaserud D. J et. al; "Gel Permeation Chromatography Coupled to Fourier Transform Mass Spectrometry for Polymer Characterization"; Anal. Chem. 1999, 71, 4793-4799. Preferred embodiments of this present disclosure subject are therefore exemplified in that the anionic polymer has a mean molecular weight $M_w$ from about 50,000 g/mol to about 250,000 g/mol, preferably from about 80,000 g/mol to about 220,000 g/mol, more preferably from about 100,000 g/mol to about 200,000 g/mol, in particular from about 110,000 g/mol to about 180,000 g/mol.

Preferred cosmetic agents as contemplated herein contain the at least one anionic polymer b) in a total amount from about 1.0 to about 8.0% by weight, preferably from about 1.5 to about 7.0% by weight, more preferably from about 1.5 to about 6.0% by weight, in particular from about 1.5 to about 5.0% by weight, based on the total weight of the composition. The use of these amounts of the anionic polymer results in a long-lasting and water-resistant styling and temporary hair coloring, without, however, negatively affecting the cleaning performance or leading to a clumping of the particulates used and thus to blockage of the aerosol nozzle.

The cosmetic agent as contemplated herein contains at least one foaming agent as a third essential component c). In principle, all gases approved for use in cosmetic agents may be used as foaming agents. However, the use of certain gases has proven to be advantageous in terms of the complete emptying of the aerosol container. Preferred embodiments of the first present disclosure subject are therefore exemplified in that the at least one foaming agent c) is selected from the group of propane, propane/butane mixtures and dimethyl ether, in particular from the group of propane/butane mixtures.

In order to ensure a good applicability and to be able to apply a sufficient amount of the composition to the hair, it has proven to be advantageous when the foaming agent is used in certain quantitative ranges. It is therefore preferred as contemplated herein when the composition contains the at least one foaming agent c), in particular propane/butane mixtures, in a total amount from about 80 to about 96% by weight, preferably from about 82 to about 94% by weight, more preferably from about 84 to about 93% by weight, in particular from about 86 to about 92% by weight, respectively based on the total weight of the composition.

In order to avoid clogging of the aerosol nozzles due to clumping of the particulates a) when water is introduced, it is particularly preferred as contemplated herein when the composition contains no alkaline compounds for neutralizing the anionic polymer b). "Alkaline compounds" as contemplated herein are understood to mean all compounds which are capable of forming hydroxide ions in water or of acting as proton acceptors. These include in particular alkali and alkaline earth metal hydroxides, alkali metal and alkaline earth metal carbonates, ammonia and organic amines. Because when this polymer is neutralized by alkaline compounds, water is released or entrained, which leads to a clumping of the particulates a) and thus to a clogging of the aerosol nozzle. Consequently, complete emptying of the container is no longer possible. In the present disclosure, "no alkaline compounds" means that they are contained in a total amount of about 0% by weight based on the total weight of the composition. Particularly preferred embodiments of the first present disclosure subject are therefore exemplified in that the composition contains no alkaline compounds, in particular no organic amines and/or hydroxides.

The clogging of the aerosol nozzle can also be avoided if the compositions as contemplated herein contain only a small amount of water and an anhydrous organic solvent is used as the solvent for the anionic polymer. As a result, a clumping of the particulates a) is avoided, which leads to a blockage of the nozzle and prevents complete emptying of the aerosol container. Particularly preferred compositions therefore contain water in a total amount from about 0 to about 2.0% by weight, preferably from about 0 to about 1.5% by weight, more preferably from about 0 to about 1.0% by weight, in particular from about 0 to about 0.99% by weight, respectively based on the total weight of the composition. Consequently, the foaming agent c) and the anhydrous solvent for the anionic polymer b) are used as carriers for the ingredients of the composition as contemplated herein.

The anionic polymer b) is preferably dissolved in organic solvents in order to ensure a uniform dispersibility on the hair when the composition is applied and in this way to achieve long-lasting and water-resistant styling properties. An organic solvent is preferably used in order to reduce the water entry and thus the risk of clumping of the particulates a). It is therefore preferred as contemplated herein when the composition additionally contains ethanol in a total amount from about 3.0 to about 8.0% by weight, in particular from about 4.0 to about 6.0% by weight, based on the total weight of the composition. On the one hand, the amount mentioned above is sufficient to dissolve the anionic polymer b) and to ensure a uniform distribution on the hair. On the other hand, this amount does not lead to excessive moistening of the hair, so that a dry cleaning of the hair is made possible.

In the following tables, particularly preferred embodiments AF 1 to AF 76 of the cosmetic compositions as contemplated herein are listed (all specifications in % by weight).

|  | AF 1 | AF 2 | AF 3 | AF 4 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 5 | AF 6 | AF 7 | AF 8 |
|---|---|---|---|---|
| Particulate a), comprising | 1.0 to 10 | 1.0 to 8.0 | 1.5 to 6.0 | 1.5 to 5.0 |
| Starch a1)[1] | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 9 | AF 10 | AF 11 | AF 12 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 13 | AF 14 | AF 15 | AF 16 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Liquid silicone oil a3)[3] |  |  |  |  |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 17 | AF 18 | AF 19 | AF 20 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Liquid silicone oil a3)[3] |  |  |  |  |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 21 | AF 22 | AF 23 | AF 24 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b)[4] | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 25 | AF 26 | AF 27 | AF 28 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b)[5] | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |

|  | AF 29 | AF 30 | AF 31 | AF 32 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |

|  | AF 33 | AF 34 | AF 35 | AF 36 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Anionic polymer b)[4] | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |

|  | AF 37 | AF 38 | AF 39 | AF 40 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Liquid silicone oil a3)[3] |  |  |  |  |
| Anionic polymer b)[5] | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |

|  | AF 41 | AF 42 | AF 43 | AF 44 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 45 | AF 46 | AF 47 | AF 48 |
|---|---|---|---|---|
| Particulate a), comprising | 1.0 to 10 | 1.0 to 8.0 | 1.5 to 6.0 | 1.5 to 5.0 |
| Starch a1)[1] | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 49 | AF 50 | AF 51 | AF 52 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 53 | AF 54 | AF 55 | AF 56 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Liquid silicone oil a3)[3] |  |  |  |  |
| Anionic polymer b) | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 57 | AF 58 | AF 59 | AF 60 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b)[4] | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 61 | AF 62 | AF 63 | AF 64 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b)[5] | 1.0 to 8.0 | 1.5 to 7.0 | 1.5 to 6.0 | 1.5 to 5.0 |
| Foaming agent c) | 80 to 96 | 82 to 94 | 84 to 93 | 86 to 92 |
| Water | 0 to 2.0 | 0 to 1.5 | 0 to 1.0 | 0 to 0.99 |

|  | AF 65 | AF 66 | AF 67 | AF 68 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2) | 1.5 to 25 | 2.0 to 23 | 2.5 to 20 | 3.5 to 18 |
| Anionic polymer b) | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |
| Water | 0 to 2.0 | 0 to 1.5 | 0 to 1.0 | 0 to 0.99 |

|  | AF 69 | AF 70 | AF 71 | AF 72 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Anionic polymer b)[4] | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |
| Water | 0 to 2.0 | 0 to 1.5 | 0 to 1.0 | 0 to 0.99 |

|  | AF 73 | AF 74 | AF 75 | AF 76 |
|---|---|---|---|---|
| Particulate a), comprising | 1.0 to 10 | 1.0 to 8.0 | 1.5 to 6.0 | 1.5 to 5.0 |
| Starch a1) | 70 to 95 | 75 to 95 | 78 to 95 | 80 to 94 |
| Pigment a2)[2] | 1.5 to 25 | 2.0 to 23 | 2.5 to 20 | 3.5 to 18 |
| Liquid silicone oil a3)[3] |  |  |  |  |
| Anionic polymer b)[5] | 1.0 to 8.0 | 1.5 to 7.0 | 1.5 to 6.0 | 1.5 to 5.0 |
| Foaming agent c)[6] | 80 to 96 | 82 to 94 | 84 to 93 | 86 to 92 |
| Water | 0 to 2.0 | 0 to 1.5 | 0 to 1.0 | 0 to 0.99 |

[1] physically modified rice starch,
[2] synthetic inorganic pigment from the group of iron oxides,
[3] polydimethylsiloxane,
[4] comprising structural units of the formulas (I) to (III) with $R_1$, $R_2$ and $R_4$ each = H or $C_1$-$C_4$ alkyl group, $R_3$ = branched or unbranched, saturated or unsaturated $C_1$-$C_{12}$ alkyl group, $R_5$ = branched or unbranched, saturated or unsaturated $C_6$-$C_{14}$ alkyl group, A = O, S or NH,
[5] comprising structural units of the formulas (I) to (III) with $R_1$, $R_4$ each = H, $R_2$ = methyl group, $R_3$ = *—$CH_2$—$CH(CH_3)_2$ group, $R_5$ = *—$C(CH_3)_2$—$CH_2$—$C(CH_3)_3$ group, A = NH
[6] selected from propane/butane mixtures.

The embodiments AF 1 to AF 76 contain water in a total amount from about 0 to about 0.99% by weight, based on the total weight of the composition, and preferably about 0% by weight, based on the total weight of the respective embodiment, of alkaline compounds, in particular on organic amines and/or hydroxides. Through the use of special particulates a) in conjunction with special anionic polymers b), these embodiments have a high cleaning effect and, after the cleaning, lead to long-lasting and water-resistant styling, in particular an increased hair volume and/or hair texture, and temporary coloring effects. Thus, the use of further styling and temporary hair coloring agents can be avoided after cleaning the hair using these dry shampoos. Since the anionic polymer b) does not have to be neutralized and is soluble in organic solvents, the amount of water in these embodiments can be reduced and thus avoiding a clumping of the particulates a). As a result, these embodiments can be completely emptied from aerosol containers, since clogging of the nozzles by the clumping of the particulates a) is avoided. In addition, this improves the applicability and the cleaning performance, since a uniform application of the particulates a) to the hair is ensured.

In addition to the components described above, the cosmetic compositions as contemplated herein may contain further ingredients, in particular additional care substances.

The composition may contain, for example, at least one protein hydrolysate and/or one of its derivatives as a care substance. Protein hydrolysates are product mixtures that are obtained by acidic, alkaline or enzymatically catalyzed degradation of proteins. The term protein hydrolysates as contemplated herein is also understood to mean total hydrolysates and individual amino acids and their derivatives and mixtures of different amino acids. The molecular weight of the protein hydrolysates which can be used as contemplated herein is between about 75 daltons, the molecular weight for glycine, and about 200,000 daltons; the molecular weight is preferably from about 75 daltons to about 50,000 daltons and very particularly preferably from about 75 daltons to about 20,000 daltons.

Furthermore, at least one vitamin, a provitamin, a vitamin precursor and/or one of the derivatives may be contained as a care substance. As contemplated herein, such vitamins, provitamins and vitamin precursors which are usually assigned to the groups A, B, C, E, F and H are preferred.

Further suitable care substances are, for example, panthenol, caffeine, nicotinamide and sorbitol, and mixtures thereof.

The compositions as contemplated herein may additionally contain at least one plant extract, but also mono- or oligosaccharides and/or lipids as a care substance.

The cosmetic compositions as contemplated herein are preferably used as dry shampoos for cleaning the hair while simultaneously achieving long-lasting styling effects and temporary hair colorings.

A second subject of the present disclosure is therefore the use of a cosmetic composition as contemplated herein for the cleaning and simultaneous temporary coloring of keratinic fibers, in particular human hair.

In principle, keratin-comprising fibers are understood to mean all animal hairs, for example wool, horsehair, angora hair, furs, feathers and products or textiles made thereof. Preferably, however, the keratinic fibers are human hair.

Temporary colorings are understood to mean hair colorings which can be achieved with the aid of pigments or substantive dyes and which can be completely removed from the hair by repeated hair washing. However, this is not understood to mean hair colorations in which oxidation dye precursors are used in conjunction with oxidizing agents.

With regard to further preferred embodiments of the method as contemplated herein, in particular with regard to the cosmetic composition used there, the statements made on the compositions as contemplated herein apply mutatis mutandis.

A third subject of the present disclosure is a method for the cleaning and simultaneous temporary coloring of keratinic fibers, in particular human hair, in which the cosmetic composition as contemplated herein is applied to keratinic fibers.

The cosmetic composition is applied to these fibers for cleaning and simultaneous temporary coloring of keratinous fibers. In a further step, the composition may subsequently be at least partially removed again from the keratinic fiber. This can be done, for example, by mechanical action on the fibers, in particular by combing or brushing the fibers. Alternatively, the cosmetic composition can also be blown out of the hair, for example, by employing a hair dryer.

If the cosmetic composition is at least partially removed again from the keratinic fiber after application, the exposure time of the composition to the fibers is preferably between about 1 minute and about 10 minutes.

A preferred embodiment of this subject of the present disclosure is therefore a method, wherein the cosmetic composition is left on the hair after the application or is removed from the hair at least partially, in particular completely, after the application.

A significant advantage of the method as contemplated herein is to clean the hair while simultaneously achieving long-lasting and water-resistant styling and temporary color effects. This is achieved by the combination of the particulates a) and anionic polymer b) previously described in connection with the first subject.

With regard to further preferred embodiments of the method as contemplated herein, in particular with regard to the cosmetic composition used there, the statements made apply mutatis mutandis to the compositions as contemplated herein and the use of the present disclosure.

The subject of the present application is exemplified in particular by the following points:

1. Cosmetic composition comprising, based on its total weight,
    a) at least one particulate comprising, based on its total weight,
        a1) from about 65 to about 98% by weight of at least one starch and
        a2) from about 1.0 to about 3.0% by weight of at least one pigment,
    b) at least one anionic polymer comprising at least one structural unit of the formula (I) and at least one structural unit of the formula (II) and at least one structural unit of the formula (III)

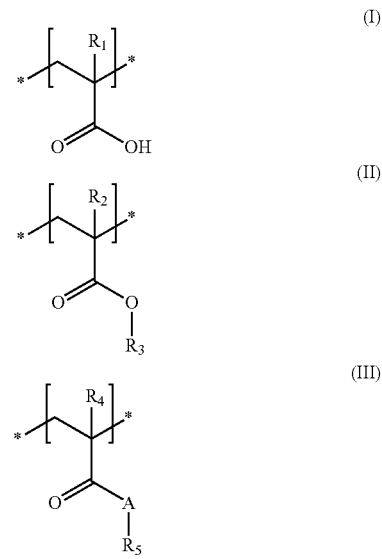

wherein
   $R_1$, $R_2$ and $R_4$, each independently of one another, stand for a hydrogen atom or a $C_1$-$C_4$ alkyl group,
   $R_3$ stands for a branched or unbranched, saturated or unsaturated $C_1$-$C_{12}$ alkyl group,
   $R_5$ stands for a branched or unbranched, saturated or unsaturated $C_6$-$C_{14}$ alkyl group,
   A stands for oxygen, sulfur or an NH group and
   c) at least one foaming agent.
2. Cosmetic composition according to point 1, exemplified in that the particulate a) contains at least one starch a1)

selected from chemically and/or physically modified rice starches, in particular from physically modified rice starch.
3. Cosmetic composition according to one of the points 1 or 2, exemplified in that the at least one particulate a) contains the at least one starch a1), in particular the physically modified rice starch, in a total amount from about 70 to about 96% by weight, in particular from about 80 to about 94% by weight, respectively based on the total weight of the particulate.
4. Cosmetic composition according to one of the preceding points, exemplified in that the at least one particulate a) contains at least one pigment a2) selected from synthetic inorganic pigments, preferably from synthetic inorganic pigments from the group of metal oxides, in particular from synthetic inorganic pigments from the group of iron oxides.
5. Cosmetic composition according to one of the preceding points, exemplified in that the at least one particulate a) contains at least one pigment a2), in particular the synthetic inorganic pigment from the group of iron oxides, in a total amount from about 1.5 to about 25% by weight, in particular from about 3.5 to about 18% by weight, respectively based on the total weight of the particulate.
6. Cosmetic composition according to one of the preceding points, exemplified in that the at least one particulate a) additionally contains at least one liquid silicone oil a3) selected from the group of dialkyl and alkylaryl siloxanes, preferably from the group of polydimethylsiloxane, cyclopentasiloxane, cyclohexasiloxane and methylphenylpolysiloxane, in particular from polydimethylsiloxanes.
7. Cosmetic composition according to point 6, exemplified in that the at least one liquid silicone oil a3), in particular polydimethylsiloxane, is present in a total amount from about 0.5 to about 5.0% by weight, in particular from about 1.5 to about 3.0% by weight, respectively based on the total weight of the particulate.
8. Cosmetic composition according to one of the preceding points, exemplified in that the at least one particulate a) additionally comprises at least one cationic surfactant a4) selected from the group of quaternary ammonium compounds, preferably from the group of cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, in particular of cetyltrimethylammonium chloride.
9. Cosmetic composition according to point 8, exemplified in that the at least one cationic surfactant a4), in particular cetyltrimethylammonium chloride, is present in a total amount from about 0.01 to about 5.0% by weight, in particular from about 0.05 to about 3.0% by weight, respectively based on the total weight of the particulate.
10. Cosmetic composition according to one of the preceding points, exemplified in that the at least one particulate a) is a particulate of the at least one starch a1) coated with the at least one pigment a2), in particular a particulate of the at least one physically modified rice starch coated with at least one synthetic inorganic pigment from the group of iron oxides.
11. Cosmetic agent according to one of the preceding points, exemplified in that the at least one particulate a) has a mean particulate size $D_{50}$ from about 1.0 μm to about 100 μm, preferably from about 5.0 μm to about 90 μm, more preferably from about 10 μm to about 80 μm, in particular from about 10 μm to about 75 μm.
12. Cosmetic composition according to one of the preceding points, exemplified in that the composition contains the at least one particulate a) in a total amount from about 1.0 to about 10% by weight, preferably from about 1.0 to about 8.0% by weight, more preferably from about 1.5 to about 6.0% by weight, in particular from about 1.5 to about 5.0% by weight, respectively based on the total weight of the composition.
13. Cosmetic composition according to one of the preceding points, exemplified in that in the structural units of the formulas (I) and (III), the radicals $R_1$ and $R_4$, in each case independently of one another, stand for a hydrogen atom and in that in the structural unit of the formula (II), the radical $R_2$ stands for a methyl group.
14. Cosmetic composition according to one of the preceding points, exemplified in that in the structural unit of the formula (II), the radical $R_3$ stands for a branched $C_3$-$C_6$ alkyl group, in particular a *—$CH_2$—$CH(CH_3)_2$ group.
15. Cosmetic composition according to one of the preceding points, exemplified in that in the structural unit of the formula (III), A stands for an NH group.
16. Cosmetic composition according to one of the preceding points, exemplified in that in the structural unit of the formula (III), the radical $R_5$ stands for a branched $C_6$-$C_{10}$ alkyl group, in particular a *—$C(CH_3)_2$—$CH_2$—$C(CH_3)_3$ group.
17. Cosmetic composition according to one of the preceding points, exemplified in that the at least one anionic polymer b) has a mean molecular weight $M_w$ from about 50,000 g/mol to about 250,000 g/mol, preferably from about 80,000 g/mol to about 220,000 g/mol, more preferably from about 100,000 g/mol to about 200,000 g/mol, in particular from about 110,000 g/mol to about 180,000 g/mol.
18. Cosmetic composition according to one of the preceding points, exemplified in that the composition contains the at least anionic polymer b) in a total amount from about 1.0 to about 10% by weight, preferably from about 1.0 to about 8.0% by weight, more preferably from about 1.5 to about 6.0% by weight, in particular from about 1.5 to about 5.0% by weight, respectively based on the total weight of the composition.
19. Cosmetic composition according to one of the preceding points, exemplified in that the at least one foaming agent c) is selected from the group of propane, propane/butane mixtures and dimethyl ether, in particular from the group of propane/butane mixtures.
20. Cosmetic composition according to one of the preceding points, exemplified in that the composition contains the at least foaming agent c) in a total amount from about 80 to about 96% by weight, preferably from about 82 to about 94% by weight, more preferably from about 84 to about 93% by weight, in particular from about 86 to about 92% by weight, respectively based on the total weight of the composition.
21. Cosmetic composition according to one of the preceding points, exemplified in that the composition contains no alkaline compounds, in particular no organic amines and/or hydroxides.
22. Cosmetic composition according to one of the preceding points, exemplified in that the composition contains water in a total amount from about 0 to about 2.0% by weight, preferably from about 0 to about 1.5% by weight, more preferably from about 0 to about 1.0% by weight, in particular from about 0 to about 0.99% by weight, respectively based on the total weight of the composition.

23. Cosmetic composition according to one of the preceding points, exemplified in that the composition additionally contains ethanol in a total amount from about 3.0 to about 8.0% by weight, in particular from about 4.0 to about 6.0% by weight, based on the total weight the composition.
24. Use of a cosmetic composition according to one of the points 1 to 23 for the cleaning and simultaneous temporary coloring of keratinic fibers, in particular human hair.
25. Method for the cleaning and simultaneous temporary coloring of keratinic fibers, in particular human hair, in which the cosmetic composition according to one of the points 1 to 23 is applied to keratinic fibers.
26. Method according to point 25, wherein the cosmetic composition is left on the hair after the application or is removed from the hair at least partially, in particular completely, after the application.

The following examples illustrate the present disclosure without, however, limiting it thereon:

EXAMPLES

The following aerosol composition was prepared.

| | Raw material | Wt % |
|---|---|---|
| 1 | Ethanol 99% denatured | 5.0 |
| 2 | Particulate a), comprising 80 to 94% by weight of starch[1] 3.5 to 18% by weight of pigment[2] 1.5 to 3.0% by weight of liquid silicone oil[3] | 6.0 |
| 3 | Anionic polymer[4] | 3.5 |
| 4 | Perfume | 0.018 |
| 5 | Propane/butane (15:85) | 85.5 |

[1] physically modified rice starch
[2] synthetic inorganic pigment from the group of iron oxides or pigment sold under the trademark Colorona ®,
[3] polydimethylsiloxane,
[4] comprising structural units of the formulas (I) to (III) with $R_1$, $R_4$ each = H, $R_2$ = methyl group, $R_3$ = *—$CH_2$—$C\underline{H}(CH_3)_2$ group, $R_5$ = *—$C(CH_3)_2$—$CH_2$—$C(CH_3)_3$ group, A = NH The composition was prepared by mixing the raw materials 1 to 4, filling up in an aerosol can and applying this can with the appropriate amount of foaming agent (raw material 5). The composition had a good applicability and excellent cleaning performance after application to the hair and brushing. Furthermore, after cleaning, an increased volume, an improved hair texture and a high temporary hair coloring could be determined. The styling and coloring effect here was water-resistant and could only be removed after the use of surfactant-comprising cleaning agents. Even after prolonged storage, no obstruction of the aerosol nozzle could be observed and the composition was completely emptied from the container.

The invention claimed is:
1. A cosmetic composition comprising,
a) particulates comprising, based on the total weight of the particulates,
a1) from 65% to 98% by weight of at least one native and/or physically modified starch, and
a2) from 1.5% to 25% by weight of at least one pigment, wherein the particulates are coated with the at least one pigment,
b) at least one anionic polymer comprising at least one structural unit of the formula (I), at least one structural unit of the formula (II), and at least one structural unit of the formula (III):

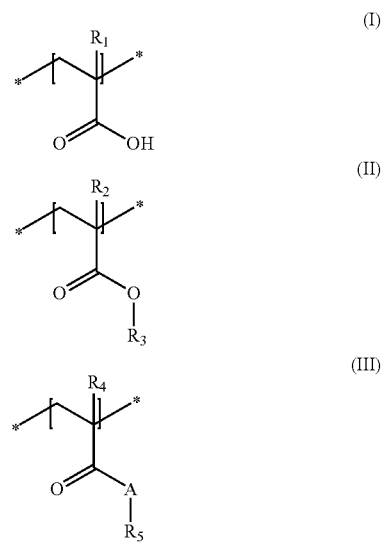

wherein
$R_1$, $R_2$ and $R_4$, each independently of one another, stand for a hydrogen atom or a $C_1$-$C_4$ alkyl group,
$R_3$ stands for a branched or unbranched, saturated or unsaturated $C_1$-$C_{12}$ alkyl group,
A stands for oxygen, sulfur or an NH group, and wherein when A stands for oxygen, $R_5$ stands for a branched or unbranched, saturated or unsaturated $C_{13}$-$C_{14}$ alkyl group, and wherein when A stands for sulfur or an NH group, $R_5$ stands for a branched or unbranched, saturated or unsaturated $C_6$-$C_{14}$ alkyl group, and
c) at least one foaming agent, wherein the cosmetic composition is free of chemically modified starch.
2. The cosmetic composition according to claim 1, wherein the at least one native and/or physically modified starch a1) is selected from native and/or physically modified rice starch.
3. The cosmetic composition according to claim 1, wherein the at least one pigment a2) is selected from synthetic inorganic pigments.
4. The cosmetic composition according to claim 1, wherein the cosmetic composition comprises the particulates a) in a total amount from 1.0% to 10% based on the total weight of the cosmetic composition.
5. The cosmetic composition according to claim 1, wherein in the structural unit of the formula (II), the radical $R_3$ stands for a branched $C_3$-$C_6$ alkyl group.
6. The cosmetic composition according to claim 1, wherein in the structural unit of the formula (III), the radical $R_5$ stands for a branched $C_6$-$C_{10}$ alkyl group.
7. The cosmetic composition according to claim 1, wherein the cosmetic composition comprises the at least one anionic polymer b) in a total amount from 1.0% to 10% based on the total weight of the cosmetic composition.
8. The cosmetic composition according to claim 1, wherein the cosmetic composition comprises the at least one foaming agent c) in a total amount from 80% to 96% based on the total weight of the cosmetic composition.
9. A method for cleaning and simultaneous temporary coloring of keratinic fibers comprising applying the cosmetic composition according to claim 1 to keratinic fibers.
10. The cosmetic composition according to claim 1, wherein the at least one native and/or physically modified starch is physically modified rice starch.

11. The cosmetic composition according to claim 1, wherein the at least one pigment a2) is selected from synthetic inorganic pigments from the group of metal oxides.

12. The cosmetic composition according to claim 1, wherein the at least one pigment a2) is selected from synthetic inorganic pigments from the group of iron oxides.

13. The cosmetic composition according to claim 1, wherein in the structural unit of the formula (II), the radical $R_3$ is $CH_2$—$CH(CH_3)_2$ group.

14. The cosmetic composition according to claim 1, wherein in the structural unit of the formula (III), the radical $R_5$ is $C(CH_3)_2$—$CH_2$—$C(CH_3)_3$ group.

15. The cosmetic composition according to claim 1, wherein the particulates a) further comprises from 0.5% to 5.0% by weight of at least one liquid silicone oil a3), based on the total weight of the particulates a).

16. The cosmetic composition according to claim 15, wherein the particulates a) further comprises from 0.01% to 1.0% by weight of at least one cationic surfactant a4) selected from the group of quaternary ammonium compounds, based on the total weight of the particulates a).

17. The cosmetic composition according to claim 16, wherein the at least one native and/or physically modified starch a1) is from 70% to 96% by weight of physically modified rice starch, and wherein the at least one pigment a2) is from 1.5% to 25% by weight of synthetic inorganic pigment from the group of iron oxides, and wherein the at least one liquid silicone oil a3) is from 1.5% to 3.0% by weight of polydimethylsiloxane, and wherein the at least one cationic surfactant a4) is from 0.05% to 0.5% by weight of cetyltrimethylammonium chloride.

18. The cosmetic composition according to claim 17, wherein the particulates a) have a mean particulate diameter of from 5.0 microns to 20 microns as measured by dynamic light scattering.

19. A cosmetic composition consisting of, based on the total weight of the cosmetic composition,
   a) particulates present in a total amount of from 1.0% to 10% by weight and consisting of, based on the total weight of the particulates,
      a1) from 65% to 98% by weight of at least one native and/or physically modified starch,
      a2) from 1.5% to 25% by weight of at least one pigment, wherein the particulates are coated with the at least one pigment,
      a3) from 0.5% to 5.0% by weight of at least one liquid silicone oil, and
      a4) from 0.01% to 1.0% by weight of at least one cationic surfactant,
   b) at least one anionic polymer that is present in a total amount of from 1.0% to 8.0% by weight and that comprises at least one structural unit of the formula (I), at least one structural unit of the formula (II), and at least one structural unit of the formula (III):

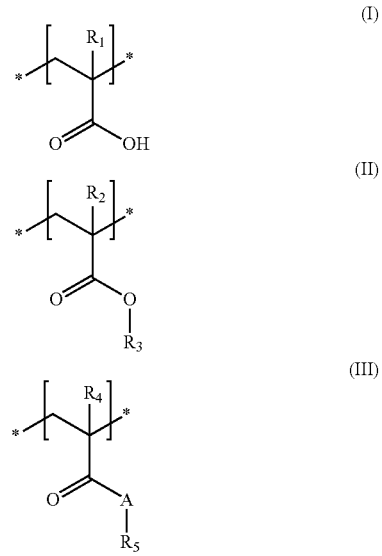

wherein
$R_1$, $R_2$ and $R_4$, each independently of one another, stand for a hydrogen atom or a $C_1$-$C_4$ alkyl group,
$R_3$ stands for a branched or unbranched, saturated or unsaturated $C_1$-$C_{12}$ alkyl group,
   A stands for oxygen, sulfur or an NH group, and wherein when A stands for oxygen, $R_5$ stands for a branched or unbranched, saturated or unsaturated $C_{13}$-$C_{14}$ alkyl group, and wherein when A stands for sulfur or an NH group, $R_5$ stands for a branched or unbranched, saturated or unsaturated $C_6$-$C_{14}$ alkyl group,
   c) at least one foaming agent present in a total amount of from 80% to 96% by weight,
   d) water that is present in a total amount of from 0 to 2.0% by weight,
   e) optionally at least one organic solvent that, if present, is in a total amount of from 3.0% to 8.0% by weight, and
   f) optionally at least one care substance selected from the group of protein hydrolysates, vitamins, provitamins, vitamin precursors, panthenol, caffeine, nicotinamide, sorbitol, plant extracts, monosaccharides, disaccharides, oligosaccharides, and lipids.

20. The cosmetic composition of claim 1, wherein the particulates have a mean particulate diameter of from 0.5 microns to 50 microns as measured by dynamic light scattering.

* * * * *